United States Patent [19]

French et al.

[11] 4,091,655

[45] May 30, 1978

[54] METHOD AND APPARATUS FOR ANALYZING TRACE COMPONENTS USING A CRYOPUMPABLE REAGENT GAS

[75] Inventors: John Barry French; Neil M. Reid, both of Thornhill; Janette A. Buckley, Willowdale, all of Canada

[73] Assignee: The Governing Counsel of the University of Toronto, Toronto, Canada

[21] Appl. No.: 790,213

[22] Filed: Apr. 25, 1977

Related U.S. Application Data

[63] Continuation-in-part of Ser. No. 555,202, Mar. 3, 1975, Pat. No. 4,023,398.

[51] Int. Cl.² ............................................. G01N 31/04
[52] U.S. Cl. .......................................... 73/23; 250/282
[58] Field of Search .................. 73/23, 23.1; 55/2, 11, 55/102, 135, 269, 270; 250/281, 282, 283, 284, 288, 289; 62/55.5

[56] References Cited

U.S. PATENT DOCUMENTS

| | | | |
|---|---|---|---|
| 3,786,249 | 1/1974 | Anbar et al. | 73/23.1 |
| 3,920,987 | 11/1975 | Anbar et al. | 250/281 |
| 4,025,790 | 5/1977 | Jetter et al. | 55/2 |
| 4,039,828 | 8/1977 | Pokar et al. | 250/288 |

*Primary Examiner*—Richard C. Queisser
*Assistant Examiner*—Stephen A. Kreitman
*Attorney, Agent, or Firm*—Rogers, Bereskin & Parr

[57] ABSTRACT

A method of analyzing a trace gas, in which the trace gas is transported in a carrier gas stream into a reaction chamber where the trace gas is ionized. The carrier gas includes or is a reagent gas which is ionized in the reaction chamber and the ions of which in turn form trace gas ions. The carrier gas, which is cryopumpable, is then injected with the trace gas ions into a vacuum chamber, the walls of which are cooled to cryopump the reagent gas and thus strip it away from the trace gas ions. The trace gas ions are focussed into an analyzer and analyzed.

5 Claims, 3 Drawing Figures

METHOD AND APPARATUS FOR ANALYZING TRACE COMPONENTS USING A CRYOPUMPABLE REAGENT GAS

This application is a continuation-in-part of our pending U.S. patent application Ser. No. 555,202 filed Mar. 3, 1975 entitled "Apparatus for Analyzing Trace Components", now U.S. Pat. No. 4,023,398.

This invention relates to methods and apparatus for analyzing trace components. The invention is typically used in connection with the detection and analysis of trace components by an analyzer such as a mass spectrometer. Trace components of the kind to be processed by the invention may be found in sample streams such as the output from a gas chromatograph.

In order to analyze a sample in a mass spectrometer or other analyzer, the sample must normally be ionized and transferred into a vacuum chamber which the mass spectrometer or other analyzer normally requires for operation. When the sample is limited in quantity, difficulties have been experienced in providing a sufficient number of sample ions to create an adequate signal. In addition, because of the limited capabilities of conventional vacuum pumps, transfer of an adequate number of sample ions (or molecules) into the vacuum chamber has been difficult and expensive.

According to the invention a chemical reagent gas is provided and is ionized and is then used to ionize the molecules of the trace gas to be analyzed. The reagent gas is cryogenically pumpable, and cryogenic pumping is used to evacuate the vacuum chamber. The use of cryogenic pumping allows an extremely high pumping rate and therefore allows use of a relatively large orifice for passage of the ions into the vacuum chamber, thereby increasing the sensitivity of the apparatus. In a preferred embodiment of the invention, staged cryopumping is used, as will be explained, to improve the efficiency of the pumping.

Further objects and advantages of the invention will appear from the following description, taken together with the accompanying drawings, in which.

Figure 1:
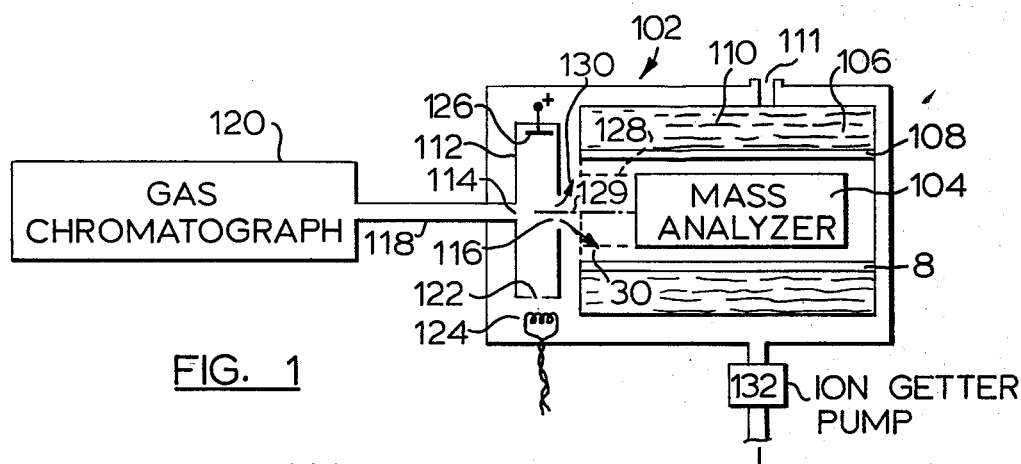
FIG. 1 is a diagrammatic view showing a first embodiment of the invention.

Reference is first made to FIG. 1, which shows a vacuum chamber diagrammatically indicated at 102 and containing a mass spectrometer 104. The interior of the vacuum chamber is indicated as being provided with a cooling fluid reservoir 106 having inwardly extending cooling fins 108. The reservoir 106 conveniently contains liquid nitrogen 110 which enters the reservoir via inlet 111. The fins 108 are formed with appropriate trapping surface geometry, as is well known in the art of cryopumping, to maximize the trapping and depositing of gas molecules. By this means, an equivalent pumping speed of hundreds of thousands of liters per second can be achieved, so that an operating vacuum in the $10^{-5}$ to $10^{-6}$ torr range (suitable for mass spectrometry) can be obtained with a relatively large entry orifice of the vacuum chamber.

The vacuum chamber 102 of FIG. 1 is provided with a hood 112 having an inlet 114 and an outlet 116. Connected to the inlet 114 is an inlet conduit 118 through which is fed a cryopumpable chemical reagent carrier gas containing the trace gas to be analyzed. The feed to conduit 118 may for example be the effluent of a gas chromatograph 120 which uses for example isobutane as a carrier.

The hood 112 includes a small orifice 122 through which electrons are directed from a filament 124, the electrons being captured by plate 126. The hood 112 and associated parts form a standard chemical ionization source, except that the outlet orifice 116, and hence the ion flow, may be made several hundred times larger than has been previously possible, through cryopumping the reagent carrier gas.

In operation, the electrons from the filament 124 ionize molecules of the reagent gas, and the reagent gas ions then transfer their charge to molecules of the trace gas from the gas chromatograph 120. The ionized trace gas, together with the reagent gas, then passes through the orifice 116 into the vacuum chamber 102.

In the vacuum chamber 102, the trace gas ions are directed into the mass spectrometer by an electrostatic lens diagrammatically indicated at 128. The path of the ions is indicated by chain dotted line 129. The reagent gas expands in a free jet, indicated by arrows 130, away from the path of the ions, and is condensed on the cryopumping surfaces 108 in the vacuum chamber. A small additional vacuum pump 132 can be provided to remove non-condensible impurities (such as nitrogen) from the vacuum chamber.

If desired, instead of using liquid nitrogen as a cooling medium, the cryopumping surfaces 108 in the vacuum chamber may be cooled by connection to suitable refrigeration apparatus presently commercially available. In this manner the cryopumping surfaces 108 may be cooled to 20° K, sufficient to condense nitrogen, and remaining impurities such as hydrogen and helium may be removed by a secondary vacuum pump or any other desired means.

In the operation of the FIG. 1 apparatus, the pressure inside the hood 112 (which constitutes an ionization chamber) is typically maintained at between 0.2 and 5 torr. The pressure is controlled, even though the outlet orifice 16 is of substantial area, by ensuring that a sufficiently high flow of material is directed into the duct 118.

In some circumstances, it may be preferred to conduct the chemical ionization at atmospheric pressure. In that event, the FIG. 2 apparatus may be used. The FIG. 2 apparatus is a modification of the FIG. 1 apparatus, and in FIG. 2 corresponding reference numerals indicate parts corresponding to those of the FIG. 1 apparatus. Again, it will be realized that the cryopumping surfaces in the vacuum chamber 102 can if desired be cooled by commercially available refrigeration apparatus, rather than by liquid nitrogen.

Figure 2:
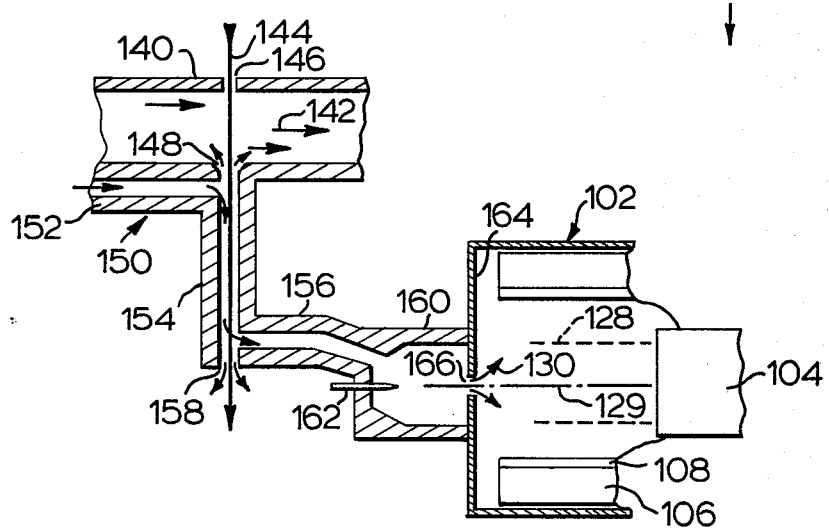
FIG. 2 is a diagrammatic view showing a second embodiment of the invention.

In the FIG. 2 apparatus, an air or other gas stream containing the trace materials to be analyzed is passed through a duct 140 as indicated by arrows 142. A wire 144 is fed through openings 146, 148 in the duct 140, and the trace materials to be analyzed are adsorbed onto the surface of the wire in conventional manner.

When the wire 144 leaves the duct 140, it then passes through a carrier gas duct 150. Specifically, the carrier gas duct 150 includes an inlet section 152 which receives a carrier gas such as argon (typically heated to between 150° C and 200° C), a desorption section 154, and an exit section 156. The carrier gas is fed into the inlet section 152 at a pressure higher than that in the duct 140, so that some of the carrier gas diffuses out through the opening 148 to prevent entry of the air or other gas into the duct 178.

In the desorption section 154, the heated carrier gas causes materials which have been adsorbed onto the wire 144 to be desorbed. The desorbed trace materials are inducted into the carrier stream. As an alternative to heating the carrier gas, the wire 144 may be electrically heated in the section 154 (by current applied through contact rollers, not shown) to desorb the trace elements which the wire has picked up.

The wire 144 leaves the desorption section 154 through opening 158, which again is sealed from the atmosphere by the excess pressure of the carrier gas in duct 150. The bulk of the carrier gas, containing the trace material to be analyzed, enters an ionization chamber 160 fitted with an electric discharge needle 162. The needle 162 is connected to a source of potential (not shown) to create a corona in the chamber 160. The carrier gas contains a suitable reagent gas (e.g. isobutane) which is ionized by the corona. The reagent ions then react with molecules of the trace gas to form trace ions.

The reaction chamber 160 is separated from the vacuum chamber 102 by a metal plate 164, which forms a dividing wall. The plate 164 is insulated from the discharge needle 162 and is connected to a source of appropriate attractive potential (not shown) relative to the needle 162, to drift the trace ions toward the plate 164. The plate 164 contains an opening 166 which is aligned with the axis of the needle 162 and through which a portion of the trace ions pass. Trace ions incident on the plate 164 are (depending on the temperature of the gas mixture) re-emitted as molecules and may again participate in ion-molecule reactions with the reagent gas and be reionized so that they will again have an opportunity to enter the vacuum chamber 102 as trace ions.

The trace ions which pass through the opening 166 are guided by the lens elements 128 into the mass spectrometer 104 or other analyzer, where they are analyzed as before. The carrier gas, including the reagent gas therein, expands in a free jet indicated by arrows 130, as before, away from the path 129 of the ions, and is condensed in the cooled encircling walls of the vacuum chamber.

The sample gas, which comprises a carrier gas plus the trace components to be analyzed, may be produced in various ways other than the wire technique illustrated in FIG. 2. For example, the trace components to be analyzed may be dissolved in a solvent, e.g. air containing the trace components may be bubbled through the solvent. If the trace material is in water, then the water itself may be the solvent. Alternatively the trace may be collected on a solid substrate, e.g. charcoal, and then transferred to a solvent (e.g. benzene) by shaking the substrate in the solvent. The solvent may be benzene, methylene chloride, hexane, isooctane, or any other appropriate solvent.

The solvent, with the trace material therein, is then vaporized. This may be performed by injecting it into a stream of warm carrier gas. The solvent may be used as a chemical ionization reagent, or an additional reagent can be added as part of or can be the entire carrier gas.

The trace components may also be emitted from a liquid chromatograph. In this case the liquid carrier will be vaporized before ionization. In all of the above cases, the carrier gas, containing the trace components and also containing any desired reagent gases, will be injected directly through a conduit such as conduit 156, into the reaction chamber 160.

Typical cryopumpable chemical ionization reagent gases which may be used in the FIGS. 1 and 2 apparatus are water vapour ($H_2O$), lower molecular weight hydrocarbons such as isobutane, benzene, methylene chloride, hexane, isooctane, or other appropriate reagents. All will preferably have a vapour pressure of substantially less than atmospheric pressure at a temperature to which the walls of the vacuum chamber can be conveniently cooled. For example they may have a vapour pressure of $10^{-4}$ torr or less at the temperature to which the vacuum chamber walls are cooled.

Figure 3:
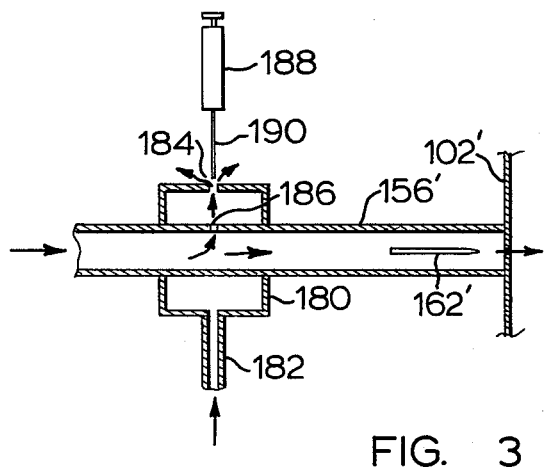
FIG. 3 is a sectional view showing a method of introducing a sample.

Another method of injecting a sample containing the trace components is shown in FIG. 3, in which primed reference numerals indicate parts corresponding to those of FIG. 2. In FIG. 3 the conduit 156' is encircled by an outer annular plenum 180 which is independantly supplied with cryopumpable carrier gas via duct 182. The plenum 180 contains an aperture 184 in the outer wall, aligned with a corresponding aperture 186 in the duct 156'. The flow of carrier gas into plenum 180 is kept high enough so that some carrier gas effuses out opening 184 and prevents entry of air into the plenum. Preferably however the flow is such relative to the flow in conduit 156' that gas from conduit 156' effuses out through opening 186 into the plenum. The sample, contained in a syringe 188, is injected by inserting the syringe tip 190 through openings 184, 186 into the duct 156' and depressing the syringe plunger. This eliminates the need for a septum or rubber membrane through which the syringe is inserted and hence eliminates an important source of contamination. The liquid sample is vapourized in the warm carrier gas in duct 156'. Ionization of the sample may be carried out by chemical ionization using a reagent gas, as before, or it may be carried out by other convenient means (e.g. by ionizing radiation from a foil or electric discharge acting directly on the sample).

Typical carrier gases (other than chemical reagent gases) which may be used depending on the temperature to which the vacuum chamber walls are cooled, are nitrogen, argon, carbon dioxide, oxygen (the latter for use with positive ions only), and appropriate freon gases. Even clean air may be used as a carrier gas, provided that the vacuum chamber is adequately cooled (to 20° K or less). Again all of the carrier gases will preferably have a vapour pressure of $10^{-4}$ torr or less at a temperature of which the walls of the vacuum chamber 2 can be conveniently cooled.

What we claim is:

1. A method of analyzing a trace gas, comprising:
    (1) introducing a reagent gas and said trace gas into a first region, said reagent gas being of the kind having a vapour pressure substantially less than atmospheric at a predetermined temperature and ions of said reagent gas being reactive with molecules of said trace gas to form trace gas ions,
    (2) forming ions from said reagent gas in said first region and thereby forming ions of said trace gas,
    (3) transporting said trace ions, with at least some of said reagent gas, into a vacuum chamber,
    (4) cooling a surface in said vacuum chamber to below said predetermined temperature, so that said reagent gas will condense on said wall,
    (5) guiding said ions of said trace gas along a selected path in said vacuum chamber, said path being spaced from said surface, and (6) analyzing said ions of said trace gas.

2. A method according to claim 1 wherein the step (1) includes the step of transporting said trace molecules into said first region in a carrier gas, said carrier gas being of the kind having a vapour pressure substantially less than atmospheric at said predetermined temperature, said reagent gas being a part of said carrier gas.

3. A method according to claim 1 including the step of dissolving in a solvent the trace material to be analyzed, then vapourizing said solvent to form a mixture of solvent and trace gases, and wherein the step (1) includes the step of introducing said mixture into said first region, the solvent gas being of the kind having a vapour pressure substantially less than atmospheric at said predetermined temperature, the step (3) including the step of transporting at least some of said solvent gas into said chamber.

4. A method according to claim 3 wherein said solvent is of a kind the ions of which are reactive with molecules of said trace gas to form trace gas ions, said solvent gas thereby constituting at least a part of said reagent gas.

5. A method according to claim 1 wherein said reagent gas is selected from the group consisting of water vapour, isobutane, benzene, methylene chloride, hexane and isooctane.

* * * * *